United States Patent

Umezu

Patent Number: 6,166,246
Date of Patent: Dec. 26, 2000

[54] 4-FLUOROSALICYCLIC ACID DERIVATIVE AND PROCESS FOR PRODUCTION THEREOF

[75] Inventor: Kazuto Umezu, Shizuoka-ken, Japan

[73] Assignee: Ihara Chemical Industry Co., Ltd., Tokyo, Japan

[21] Appl. No.: 09/091,249

[22] PCT Filed: Oct. 17, 1997

[86] PCT No.: PCT/JP97/03761

§ 371 Date: Jun. 12, 1998

§ 102(e) Date: Jun. 12, 1998

[87] PCT Pub. No.: WO98/17620

PCT Pub. Date: Apr. 30, 1998

[30] Foreign Application Priority Data

Oct. 18, 1996 [JP] Japan ................................. 8-297312

[51] Int. Cl.⁷ .................................................. C07C 65/10
[52] U.S. Cl. .......................................... 562/477; 562/405
[58] Field of Search .................................. 562/405, 477

[56] References Cited

U.S. PATENT DOCUMENTS

| | | | |
|---|---|---|---|
| 3,337,616 | 8/1967 | Kaeding et al. | 556/115 |
| 3,689,536 | 9/1972 | Majewski et al. | 562/477 |
| 3,928,470 | 12/1975 | Soula et al. | 568/708 |
| 4,131,618 | 12/1978 | Weinstock et al. | 562/469 |
| 4,232,172 | 11/1980 | Becher et al. | 562/423 |
| 4,827,027 | 5/1989 | Cocco | 562/477 |
| 5,266,674 | 11/1993 | Yu | 528/226 |
| 5,270,308 | 12/1993 | Shiraishi et al. | 514/229.8 |

FOREIGN PATENT DOCUMENTS 7-501330  2/1995  Japan .
9-77716   3/1997  Japan .

OTHER PUBLICATIONS

H. Duda et al., "Halosalicylohydroxamic acids. I. Dihalosalicylohydroxamic acids.", Chemical Abstracts, vol. 63, No. 12, pp. 16255–16256, Dec. 6, 1965.

Primary Examiner—Paul J. Killos
Assistant Examiner—Taylor V. Oh
Attorney, Agent, or Firm—Kubovcik & Kubovcik

[57] ABSTRACT

The present invention provides a 4-fluorosalicylic acid derivative represented by the following general formula (1):

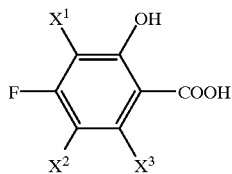

(1)

(wherein $X^1$, $X^2$ and $X^3$ are each independently a hydrogen atom or a halogen atom with a proviso that there is no case in which all of $X^1$, $X^2$ and $X^3$ are hydrogen atoms or fluorine atoms simultaneously); and a process for producing the above 4-fluoro-salicylic acid derivative.

The 4-fluorosalicylic acid derivative of the present invention is a novel compound not described in any literature and is very suitable as a raw material for production of a 3-fluorophenol derivative (the 3-fluorophenol derivative is very useful as an intermediate for liquid crystal, recording material, medicine and agricultural chemical) because the 4-fluorosalicylic acid derivative can be easily converted to the 3-fluorophenol derivative.

2 Claims, No Drawings

4-FLUOROSALICYCLIC ACID DERIVATIVE AND PROCESS FOR PRODUCTION THEREOF

TECHNICAL FIELD

The present invention relates to a novel 4-fluorosalicylic acid derivative which can be easily converted to a 3-fluorophenol derivative very useful as an intermediate for liquid crystal, recording material, medicine, agricultural chemical, etc., as well as to a process for production of said 4-fluorosalicylic acid derivative.

BACKGROUND ART

The 4-fluorosalicylic acid derivative of the present invention is a novel compound which has been unknown and which is not described in any literature. It has been also unknown that the 4-fluorosalicylic acid derivative can become a useful raw material for producing a 3-fluorophenol derivative useful as an intermediate for liquid crystal [refer to Japanese Patent Application Kokai (Laid-Open) No. 291899/1995 and Japanese Patent Application Kokai (Laid-Open) No. 10847/1995], recording material [refer to Japanese Patent Application Kokai (Laid-Open) No. 264587/1991], agricultural chemical [refer to Japanese Patent Application Kokai (Laid-Open) No. 345740/1994], medicine [refer to Japanese Patent Application Kokai (Laid-Open) No. 309837/1995], etc.

The objects of the present invention are to provide a novel 4-fluorosalicylic acid derivative which can be easily converted to a 3-fluorophenol derivative useful as mentioned above, and a process for producing the 4-fluorosalicylic acid derivative.

The present inventors made a study in order to achieve the above objects. As a result, the present inventors found out that a useful 3-fluorophenol derivative can be easily produced by decarboxylation of a 4-fluorosalicylic acid derivative and that the 4-fluorosalicylic acid derivative used as a raw material in the decarboxylation is a novel compound not described in any literature and is useful not only as an intermediate in production of the 3-fluorophenol derivative but also in production of liquid crystals, etc. The present invention has been completed based on the above finding.

DISCLOSURE OF THE INVENTION

The present invention provides a 4-fluorosalicylic acid derivative represented by the following general formula (1):

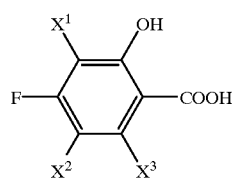

(1)

(wherein $X^1$, $X^2$ and $X^3$ are each independently a hydrogen atom or a halogen atom with a proviso that there is no case in which all of $X^1$, $X^2$ and $X^3$ are hydrogen atoms or fluorine atoms simultaneously).

The present invention also provides a process for producing a 4-fluorosalicylic acid derivative represented by the following general formula (1):

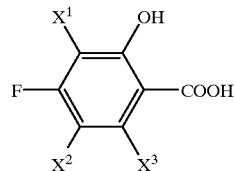

(1)

(wherein $X^1$, $X^2$ and $X^3$ are each independently a hydrogen atom or a halogen atom with a proviso that there is no case in which all of $X^1$, $X^2$ and $X^3$ are hydrogen atoms or fluorine atoms simultaneously), which process comprises reacting a 2,4-difluorobenzoic acid derivative represented by the following general formula (4):

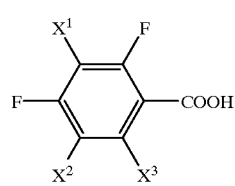

(4)

(wherein $X^1$, $X^2$ and $X^3$ are each independently a hydrogen atom or a halogen atom with a proviso that there is no case in which all of $X^1$, $X^2$ and $X^3$ are hydrogen atoms or fluorine atoms simultaneously) with an alkali metal hydroxide in at least one solvent selected from the group consisting of a compound represented by the following general formula (2):

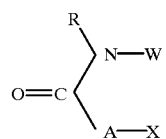

(2)

[wherein A is a group —$CH_2$— or a group —NR'— (wherein R' is a lower alkyl group); R is a lower alkyl group; W is a lower alkyl group; X is a hydrogen atom or a lower alkyl group when A is a group —$CH_2$—, and is a lower alkyl group when A is a group —NR'—; W and X may combine with each other to form a lower alkylene group and become a 5- to 7-membered ring together with —N—C—A—] and a compound represented by the following general formula (3):

Y—Q—Z (3)

(wherein Q is a group —SO— or a group —$SO_2$—; Y and Z are each independently a lower alkyl group; Y and Z may combine with each other to form a lower alkylene group and become a 4- to 6-membered ring together with a group —SO— or a group —$SO_2$—).

BEST MODE FOR CARRYING OUT THE INVENTION

The present invention is hereinafter described in detail.

The compound of the present invention is a 4-fluorosalicylic acid derivative represented by the above-mentioned general formula (1). In the general formula (1), the substituents represented by $X^1$, $X^2$ and $X^3$ are each independently a hydrogen atom or a halogen atom with a proviso that there is no case in which all of $X^1$, $X^2$ and $X^3$ are hydrogen atoms or fluorine atoms simultaneously. Here, the halogen atoms refer to a fluorine atom, a chlorine atom and a bromine atom. The compound represented by the general formula (1) can be exemplified by 3,4-difluorosalicylic acid, 5-chloro-4-fluorosalicylic acid, 3,5-dichloro-4-fluorosalicylic acid, 4,6-difluorosalicylic acid, 3,4,5-trifluorosalicylic acid and 4,5-difluorosalicylic acid.

The compound of the present invention can be produced, for example, by the following process of the present invention.

That is, a 2,4-difluorobenzoic acid derivative represented by the following general formula (4):

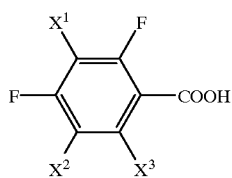

(4)

(wherein $X^1$, $X^2$ and $X^3$ are each independently a hydrogen atom or a halogen atom with a proviso that there is no case in which all of $X^1$, $X^2$ and $X^3$ are hydrogen atoms or fluorine atoms simultaneously) is reacted with an alkali metal hydroxide in at least one solvent selected from the group consisting of a compound represented by the following general formula (2):

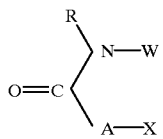

(2)

[wherein A is a group —CH$_2$— or a group —NR'— (wherein R' is a lower alkyl group); R is a lower alkyl group; W is a lower alkyl group; X is a hydrogen atom or a lower alkyl group when A is a group —CH$_2$—, and is a lower alkyl group when A is a group —NR'—; W and X may combine with each other to form a lower alkylene group and become a 5- to 7-membered ring together with —N—C—A—] and a compound represented by the following general formula (3):

Y—Q—Z (3)

(wherein Q is a group —SO— or a group —SO$_2$—; Y and Z are each independently a lower alkyl group; Y and Z may combine with each other to form a lower alkylene group and become a 4- to 6-membered ring together with a group —SO— or a group —SO$_2$—). After the completion of the reaction, the reaction mixture is subjected to an ordinary post-treatment such as precipitation by acidification or the like, whereby the present invention compound can be isolated.

The compound used as a solvent in the process of the present invention is a compound represented by the general formula (2) or a compound represented by the general formula (3). In the general formula (2), the lower alkyl groups represented by the substituents R, R', W and X (X may be a hydrogen atom) are each independently an alkyl group having 1 to 4 carbon atoms, such as methyl group, ethyl group, n-propyl group, isopropyl group, n-butyl group, isobutyl group or the like; and the lower alkylene group formed when the substituents W and X combine with each other, is an alkylene group having 2 to 4 carbon atoms, such as ethylene group, trimethylene group, tetramethylene group or the like.

Also in the general formula (3), the lower alkyl groups represented by the substituents Y and Z are each independently an alkyl group having 1 to 4 carbon atoms, such as methyl group, ethyl group, n-propyl group, isopropyl group, n-butyl group, isobutyl group or the like; and the lower alkylene group formed when the substituents Y and Z combine with each other, is an alkylene group having 3 to 5 carbon atoms, such as trimethylene group, tetramethylene group, pentamethylene group or the like.

Of the compounds represented by the general formula (2) or (3), those preferable as the solvent used in the process of the present invention are 1,3-dimethyl-2-imidazolidinone, 1-methyl-2-pyrrolidone, 1,3-dimethyl-3,4,5,6-tetrahydro-2 (1H)-pyrimidinone, dimethyl sulfoxide, N,N-diethylacetamide, 1,1,3,3-tetramethylurea, tetramethylene-sulfone and dimethylsulfone.

The amount of the solvent used can be at least an amount enabling stirring during the reaction, but is usually 0.1 to 6 litter, preferably 0.3–3 litter per mole of the 2,4-difluorobenzoic acid derivative represented by the general formula (4).

The alkali metal hydroxide used in the process of the present invention can be exemplified by lithium hydroxide, sodium hydroxide and potassium hydroxide. Of these, sodium hydroxide and lithium hydroxide are preferred.

The amount of the alkali metal hydroxide used can be 2 to 6 moles, preferably 3 to 5 moles per mole of the 2,4-difluorobenzoic acid derivative.

The reaction temperature used in the process of the present invention can be determined appropriately at a temperature not higher than the boiling point of the solvent used, but is preferably 80 to 200° C., more preferably 100 to 160° C. The reaction time is usually about 2 to 12 hours. The pressure employed during the reaction may be any of atmospheric pressure, applied pressure or reduced pressure, but atmospheric pressure is employed usually.

The 4-fluorosalicylic acid derivative which is an intended product in the process of the present invention, i.e. the compound of the present invention can be isolated by subjecting the reaction mixture after the completion of the reaction to an ordinary isolation method such as precipitation by acidification and subsequent filtration, or solvent extraction and subsequent concentration of extracting solvent. The 4-fluorosalicylic acid derivative can also be taken out by filtering the reaction mixture after the completion of the reaction to separate the alkali metal salt of the product from the solvent and then subjecting the salt to precipitation by acidification.

The above-obtained 4-fluorosalicylic acid derivative (the compound of the present invention) can be used without being purified, or can be purified by being recrystallized from an alcohol-water mixed solvent or the like.
(Production of 3-fluorophenol derivative)

Next is described, for reference, a process for producing, from the 4-fluorosalicylic acid derivative (the compound of the present invention), a 3-fluorophenol derivative which is useful as an intermediate for liquid crystal, etc.

That is, the 3-fluorophenol derivative can be produced by heating the 4-fluorosalicylic acid derivative of the present invention represented by the general formula (1), in the presence of a base in the presence or absence of a solvent.

As the base, an organic base or an inorganic base can be used. As the organic base, there can be mentioned, for example, a tertiary amine (which is a nitrogen-containing organic base free from [N]—H and which is a tertiary amine in a broad sense); specific examples thereof are pyridines [e.g. pyridine and 4-(N,N-dimethylamino)pyridine (DMAP)], quinolines (e.g. quinoline), trialkylamines (e.g. triethylamine and trioctylamine) and N,N-dialkylanilines (e.g. N,N-dimethylaniline). The amount of the organic base used is 0.01 to 50 moles, preferably 0.1 to 20 moles per mole of the 4-fluorosalicylic acid derivative.

As the inorganic base, there can be used a hydroxide or carbonate of an alkali metal or an alkaline earth metal. Specific examples are hydroxides of alkali metals or alkaline earth metals (e.g. sodium hydroxide, potassium hydroxide and calcium hydroxide) and carbonates of alkali metals or alkaline earth metals (e.g. sodium carbonate, sodium hydrogencarbonate, potassium carbonate, potassium hydrogencarbonate, calcium carbonate and barium carbonate). The amount of the inorganic base used is 0.01 to 5 moles, preferably 0.1 to 2 moles per mole of the 4-fluorosalicylic acid derivative.

As the base used in the reaction, an organic base is preferred. Use of, in particular, guinoline, trioctylamine or 4-(N,N-dimethylamino)pyridine gives a favorable result.

The reaction proceeds with no problem in a solventless state, but a solvent may be used as necessary. When a solvent is used, there can be used a solvent inert to the reaction (e.g. giving rise to no side reaction with the 4-fluorosalicylic acid derivative), for example, an aprotic polar solvent, such as 1-methyl-2-pyrrolidone (NMP), 1,3-dimethyl-2-imidazolidinone (DMI), N,N-dimethylacetamide (DMAC), tetramethylsulfone or the like.

As the solvent, there can also be used an aromatic hydrocarbon or aromatic halogenated hydrocarbon such as toluene, xylene, chlorobenzene, dichlorobenzene, trichlorobenzene or the like.

In the reaction, the above-mentioned organic base may be used so as to function not only as a base but also as a solvent.

In the reaction, the amount of the solvent used is, for example, 0.3 to 3 litter, preferably 0.5 to 2 litter per mole of the 4-fluorosalicylic acid derivative.

The reaction temperature is in the range of, for example, 150 to 230° C. The reaction time is usually 1 to 20 hours, preferably 2 to 15 hours. The reaction may be carried out at atmospheric pressure, under applied pressure or under reduced pressure.

The 3-fluorophenol formed in the reaction can be taken out by a method which differs depending upon the solvent used in the reaction, for example, by a method of acid-washing the reaction mixture, separating the resulting organic layer and then subjecting the separated organic layer to concentration or rectification, or by a method of subjecting the reaction mixture to precipitation by acidification and subsequent solvent extraction and then subjecting the resulting organic layer to concentration or rectification.

The present invention is described more specifically below by way of Examples and Reference Examples.

EXAMPLE 1

1.76 g (0.01 mole) of 2,3,4-trifluorobenzoic acid, 1.62 g (0.04 mole) of powdery 99% sodium hydroxide and 20 ml of 1,3-dimethyl-2-imidazolidinone were fed into a 100-ml four-necked flask provided with a thermometer, a stirrer and a reflux condenser. The mixture was stirred at 150° C. for 2 hours to give rise to a reaction. After the completion of the reaction, part of 1,3-dimethyl-2-imidazolidinone was recovered. The resulting reaction mixture was diluted with 500 ml of water and then subjected to precipitation with a 10% aqueous hydrochloric acid solution. The resulting material was cooled in an ice bath. The resulting crystals were collected by filtration, washed with water, and dried to obtain 1.66 g of 3,4-difluorosalicylic acid. The isolated yield was 95.1% relative to the 2,3,4-trifluorobenzoic acid used.

(Properties of 3,4-difluorosalicylic acid)

Melting point: 176.8 to 178.2° C.

(Confirmation data)

MS m/z: 174 (M$^+$)

60 MHz $^1$H-NMR (DMSO-d$_6$+CDCl$_3$) δ value: 6.63–7.20 (m, 1H), 7.47–7.90 (m, 1H), 8.33 (brs, 2H)

IR (KBr tablet, cm$^{-1}$): 3431, 3211, 3104, 3079, 3022, 2942, 2864, 2677, 2546, 2343, 1658, 1573, 1540, 1512, 1470, 1445, 1384, 1316, 1277, 1214, 1200, 1149, 1054, 909, 831, 785, 716, 689, 609

EXAMPLE 2

1.93 g (0.01 mole) of 5-chloro-2,4-difluorobenzoic acid, 1.62 g (0.04 mole) of powdery 99% sodium hydroxide and 20 ml of 1-methyl-2-pyrrolidone were fed into a 100-ml four-necked flask provided with a thermometer, a stirrer and a reflux condenser. The mixture was stirred at 130° C. for 3 hours to give rise to a reaction. After the completion of the reaction, part of 1-methyl-2-pyrrolidone was recovered. The resulting reaction mixture was diluted with 500 ml of water and then subjected to precipitation with a 10% aqueous hydrochloric acid solution. The resulting crystals were collected by filtration, washed with water, and dried to obtain 1.76 g of 5-chloro-4-fluorosalicylic acid. The isolated yield was 92.1% relative to the 5-chloro-2,4-difluorobenzoic acid used.

(Properties of 5-chloro-4-fluorosalicylic acid)

Melting point: 200.0 to 201.2° C.

(Confirmation data)

MS m/z: 190 (M$^+$)

60 MHz $^1$H-NMR (DMSO-d$_6$+CDCl$_3$) δ value: 6.79 (d, 1H, J=10.3 Hz), 7.92 (d, 1H, J=8.8 Hz), 9.46 (brs, 2H)

IR (KBr tablet, cm$^{-1}$): 3630–3280, 1669, 1616, 1590, 1491, 1475, 1449, 1377, 1276, 1248, 1212, 1166, 849, 703, 611

EXAMPLE 3

2.27 g (0.01 mole) of 3,5-dichloro-2,4-difluorobenzoic acid, 1.62 g (0.04 mole) of powdery 99% sodium hydroxide and 20 ml of 1-methyl-2-pyrrolidone were fed into a 100-ml four-necked flask provided with a thermometer, a stirrer and a reflux condenser. The mixture was stirred at 130° C. for 2 hours to give rise to a reaction. Then, the same post-treatment as in Example 2 was conducted to obtain 2.07 g of 3,5-dichloro-4-fluorosalicylic acid. The isolated yield was 91.4% relative to the 3,5-dichloro-2,4-difluorobenzoic acid used.

(Properties of 3,5-dichloro-4-fluorosalicylic acid)

Melting point: 119.4 to 120.9° C.

(Confirmation data)

MS m/z: 225 (M$^+$)

60 MHz $^1$H-NMR (DMSO-d$_6$+CDCl$_3$) δ value: 7.39 (brs, 2H), 7.89 (d, 1H, J=8.2 Hz)

IR (KBr tablet, cm$^{-1}$): 3451, 3428, 1674, 1641, 1607, 1545, 1474, 1458, 1432, 1307, 1292, 1241, 1057, 810, 720, 659

EXAMPLE 4

1.76 g (0.01 mole) of 2,4,6-trifluorobenzoic acid, 1.62 g (0.04 mole) of powdery 99% sodium hydroxide and 20 ml of 1-methyl-2-pyrrolidone were fed into a 100-ml four-necked flask provided with a thermometer, a stirrer and a reflux condenser. The mixture was stirred at 130° C. for 3 hours to give rise to a reaction. Then, the same post-treatment as in Example 2 was conducted to obtain 1.47 g of 4,6-difluorosalicylic acid. The isolated yield was 84.3% relative to the 2,4,6-trifluorobenzoic acid used.

(Properties of 4,6-difluorosalicylic acid)

Melting point: 180.8 to 183.4° C.

(Confirmation data)

MS m/z: 174 (M$^+$)

60 MHz $^1$H-NMR (DMSO-d$_6$+CDCl$_3$) δ value: 6.27–6.80 (m, 2H), 7.20 (brs, 2H)

IR (KBr tablet, cm$^{-1}$): 3421, 3274, 3106, 3005, 2964, 2929, 1667, 1632, 1598, 1561, 1509, 1465, 1436, 1365, 1325, 1253, 1178, 1137, 1065, 854, 830, 787, 612

EXAMPLE 5

3.88 g (0.02 mole) of 2,3,4,5-tetrafluorobenzoic acid, 3.23 g (0.08 mole) of powdery 99% sodium hydroxide and 40 ml of 1,3-dimethyl-2-imidazolidinone were fed into a 200-ml four-necked flask provided with a thermometer, a stirrer and a reflux condenser. The mixture was stirred at 130° C. for 3 hours to give rise to a reaction. Then, the same post-treatment as in Example 1 was conducted to obtain 1.14 g of 3,4,5-trifluorosalicylic acid. The isolated yield was 29.7% relative to the 2,3,4,5-tetrafluorobenzoic acid used.

(Properties of 3,4,5-trifluorosalicylic acid)

Melting point: 75.0 to 76.8° C.

(Confirmation data)

MS m/z: 192 (M$^+$)

60 MHz $^1$H-NMR (DMSO-d$_6$+CDCl$_3$) δ value: 7.27–7.73 (m, 1H), 8.72 (brs, 2H)

IR (KBr tablet, cm$^{-1}$): 2885, 1687, 1650, 1614, 1526, 1465, 1285, 1232, 1032, 905, 775, 694.

EXAMPLE 6

1.76 g (0.01 mole) of 2,4,5-trifluorobenzoic acid, 1.62 g (0.04 mole) of powdery 99% sodium hydroxide and 20 ml of 1,3-dimethyl-2-imidazolidinone were fed into a 100-ml four-necked flask provided with a thermometer, a stirrer and a reflux condenser. The mixture was stirred at 130° C. for 3 hours to give rise to a reaction. Then, the same post-treatment as in Example 1 was conducted to obtain 0.50 g of 4,5-difluorosalicylic acid. The isolated yield was 28.7% relative to the 2,4,5-trifluorobenzoic acid used.

(Properties of 4,5-difluorosalicylic acid)

Melting point: 134.4 to 137.0° C.

(Confirmation data)

MS m/z: 174 (M$^+$)

60 MHz $^1$H-NMR (DMSO-d$_6$+CDCl$_3$) δ value: 6.60–7.00 (m, 1H), 7.27 (brs, 2H), 7.47–7.93 (m, 1H)

IR (KBr tablet, cm$^{-1}$): 3083, 1669, 1605, 1506, 1448, 1282, 1249, 1208, 1158, 897, 861, 698, 656

REFERENCE EXAMPLES 1 TO 6

0.01 mole of a 4-fluorosalicylic acid derivative and 10 ml of quinoline were fed into a 50-ml flask provided with a stirrer and a reflux condenser. The mixture was stirred for 2 hours in an oil bath of 230° C. to give rise to a reaction to convert the 4-fluorosalicylic acid derivative to a 3-fluorophenol derivative. The reaction mixture was subjected to gas chromatography and GC-MS. The results are shown in Table 1.

TABLE 1

| Reference Examples | Raw Material (4-Fluorosalicylic acid derivative) | Product (3-fluorophenol derivative) | Purity (GC total area %) | MS m/z (M+) |
|---|---|---|---|---|
| 1 | F, OH, F, COOH (structure) | F, OH, F (structure) | 96.4 | 130 |
| 2 | OH, F, COOH, F (structure) | OH, F, F (structure) | 96.7 | 130 |
| 3 | OH, F, COOH, F (structure) | OH, F, F (structure) | 96.9 | 130 |

TABLE 1-continued

| Reference Examples | Raw Material (4-Fluorosalicylic acid derivative) | Product (3-fluorophenol derivative) | Purity (GC total area %) | MS m/z (M+) |
|---|---|---|---|---|
| 4 | F, OH, F, F, COOH | F, OH, F, F | 96.9 | 148 |
| 5 | OH, F, COOH, Cl | OH, F, Cl | 94.6 | 146 |
| 6 | Cl, OH, F, Cl, COOH | Cl, OH, F, Cl | 99.8 | 180 |

INDUSTRIAL APPLICABILITY

The present invention provides a novel 4-fluorosalicylic acid derivative. The 4-fluorosalicylic acid derivative is very suitable as a raw material for production of a 3-fluorophenol derivative which is very useful as an intermediate for liquid crystal, recording material, medicine and agricultural chemical.

What is claimed is:

1. A 4-fluorosalicylic acid derivative represented by the following formula (1):

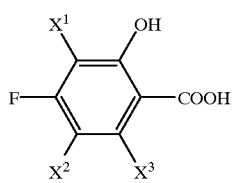

(1)

wherein $X^1$, $X^2$ and $X^3$ are each independently a hydrogen atom or a halogen atom with the proviso that there is no case in which all of $X^1$, $X^2$ and $X^3$ are hydrogen atoms or fluorine atoms and with the proviso that the compound 5-bromo-4-fluorosalicylic acid is excluded.

2. A process for producing a 4-fluorosalicylic acid derivative represented by the following formula (1):

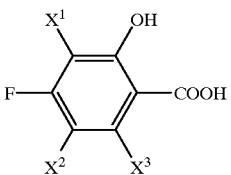

(1)

wherein $X^1$, $X^2$ and $X^3$ are each independently a hydrogen atom or a halogen atom with a proviso that there is no case in which all of $X^1$, $X^2$ and $X^3$ are hydrogen atoms or fluorine atoms, which process comprises reacting a 2,4-difluorobenzoic acid derivative represented by the formula (4):

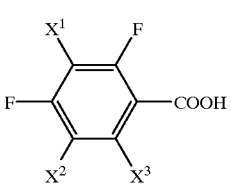

(4)

wherein $X^1$, $X^2$ and $X^3$ are each independently a hydrogen atom or a halogen atom with the proviso that there is no case in which all of $X^1$, $X^2$ and $X^3$ are hydrogen atoms or fluorine atoms, with an alkali metal hydroxide in at least one solvent selected from the group consisting of a compound represented by the following formula (2):

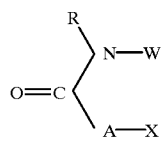 (2)

wherein A is a group —CH$_2$— or a group —NR'—, wherein R' is a lower alkyl group; R is a lower alkyl group; W is a lower alkyl group; X is hydrogen atom or a lower alkyl group when A is a group —CH$_2$—, and is a lower alkyl group when A is a group —NR'—; W and X may combine with each other to form a lower alkylene group and become a 5- to 7-membered ring together with —N—C—A—, and a compound represented by the following formula (3):

$$Y-Q-Z \qquad (3)$$

wherein Q is a group —SO— or a group —SO$_2$—; Y and Z are each independently a lower alkyl group; Y and Z may combine with each other to form a lower alkylene group and become a 4- to 6-membered ring together with a group —SO— or a group —SO$_2$—.

* * * * *